United States Patent [19]

Pomerantz

[11] Patent Number: 5,785,370
[45] Date of Patent: Jul. 28, 1998

[54] SOFT CONTACT LENS MANIPULATING DEVICE

[76] Inventor: Joseph T. Pomerantz, 405 Queen Anne Club Dr., Stevensville, Md. 21666

[21] Appl. No.: 922,516

[22] Filed: Sep. 3, 1997

[51] Int. Cl.$^6$ ............................................. A61F 9/00
[52] U.S. Cl. ............................................. 294/1.2; 294/64.1
[58] Field of Search ............................ 294/1.2, 64.1; 206/5.1; 269/21; 606/107

[56] References Cited

U.S. PATENT DOCUMENTS

| | | | |
|---|---|---|---|
| 3,091,328 | 5/1963 | Leonardos | 294/1.2 X |
| 3,583,010 | 6/1971 | Woodrum | 294/1.2 X |
| 3,647,380 | 3/1972 | Middleton | 294/1.2 X |
| 3,879,076 | 4/1975 | Barnett | 294/1.2 |
| 4,071,272 | 1/1978 | Drdlik | 294/1.2 |
| 4,332,408 | 6/1982 | Cointment | 294/1.2 |
| 5,456,508 | 10/1995 | Kozar | 294/1.2 |

*Primary Examiner*—Johnny D. Cherry

[57] ABSTRACT

A soft contact lens pickup and insertion device (10) featuring a flat, annular terminus (16) designed to engage the apex of the convex side of a soft contact lens without deforming the lens is provided together with a hollow, rigid shank (12) and a hollow, pliable vacuum actuating bulb (14). A vacuum effect generated by compressing and releasing the bulb is communicated through the adjoining shank and out upon the contiguous terminus end in order to attract and engage a soft contact lens into a position which it may subsequently be inserted upon the cornea of a user's eye.

5 Claims, 3 Drawing Sheets

SOFT CONTACT LENS MANIPULATING DEVICE

BACKGROUND

1. Field of Invention

This invention relates to the manipulation of soft contact lenses; particularly an improved, vacuum actuated device to aid in the process of grasping and applying a soft contact lens to the cornea of an eye.

2. Description of Prior Art

To date, various vacuum actuated devices have been offered to render the contact lens application process an easier and more sterile method over the conventional finger and thumb mode. However, a deficiency remains among the prior art employing the vacuum actuated process relating to the pickup and placement of soft contact lenses. The prior art does not provide a specific, efficient medium which will not cause deformation of a soft contact lens when in contact with the lens. These devices in point, employ a principle end having a concave terminus designed to seat with the convex side of a contact lens.

Several types of vacuum actuated devices using a concave end have been proposed—for example, in U.S. Pat. Nos. 3,583,010 to Woodrum (1971), 3,647,380 to Middleton (1972), 4,071,272 to Drdlik (1978), and 5,456,508 to Kozar (1995). The concave design, characteristic of the aforementioned prior art, is intended to provide a mating surface for the device to engage a contact lens. Upon engagement, the device and lens are drawn to the eye of the user for insertion of the lens upon the user's cornea. The concave ends of the prior art are provided with one state of curvature, namely concavity. These ends envelop a majority of the lens' area upon its convex side. This arrangement can be suitable for a hard contact lens due to its rigid quality, and hence, ability to resist bending if it is not engaged with the end of a device having a precise inverse shape with which to mate to the lens. Conversely, the soft contact lens must engage with the end of a device having the precise inverse shape of the lens. This condition is required of a device in order to maintain an inviolate, natural shape of the soft lens during the engagement and placement processes to ensure user success and comfort. Because of their thin and delicate character, soft contact lenses are apt to fold or collapse while in the enveloping grasp of the prior art as these devices cannot present a universal inverse shape capable of handling every soft lens that may be considered. Without a precise inverse surface with which to mate a soft lens, the prior art is rendered ineffective as it may deform the lens.

Furthermore, the prior art identified herein present the following additional disadvantages with respect to the user and manufacturer of contact lens manipulating devices:

(a) The composition of existing devices is comprised of multiple or sophisticated parts. The potential user can be dissuaded from considering the use of an aid device if the device appears to be complicated by its dependency upon multiple or sophisticated parts for actuation. The gainful mastery of the device's intended use is prolonged when the process involves these parts.

(b) In terms of manufacture, multiple or sophisticated parts can prove to be more expensive to produce and consequently less economical to the consumer.

(c) Multiple or sophisticated parts create difficulty with regular cleaning of the device; a process which is necessary in order to maintain and promote aseptic conditions considering the invasive exercise of applying contact lenses to the eyes.

OBJECTS AND ADVANTAGES

Accordingly, the specific problems as detailed in the presentation above, are obviated by the objects and advantages of the present invention as follows:

(a) to provide a novel soft contact lens manipulating device utilizing vacuum actuation which will not deform the soft lens during the engagement and placement processes thereby ensuring user success and comfort;

(b) in a preferred embodiment, to provide a device comprised of two parts only which will prevail upon the user a sense for the device that is minimally intimidating or complex and thus enable the user to benefit from an easy and an expedient mastery of its intended use;

(c) to provide, in accordance with the preceding object, a simple device relating to inexpensive manufacture thence extending economy of purchase to the consumer; and (d) to provide, in accordance with the object identified as item (b) above, a device which can avail the user with easy cleaning at frequent intervals thus maintaining and promoting an aseptic quality of the device.

A further object and advantage is to provide a device which utilizes a terminus in commission as a lens seat that envelops a minimal area of the apex of the convex side of a soft contact lens in order to prevent potential complication of the device touching the eye of the user during insertion of the lens upon the user's cornea. Still further objects and advantages will become apparent from a consideration of the ensuing drawings and description.

DRAWING FIGURES

REFERENCE NUMERALS IN DRAWINGS

| | | | |
|---|---|---|---|
| 10 | soft contact lens manipulating device | 12 | shank |
| 14 | vacuum actuating bulb | 15 | outward, annular shoulder |
| 16 | flat, annular terminus | 18 | incurvate shoulder |
| 20 | duct opening | 22 | soft contact lens |
| 30 | flat, aseptic surface | | |

SUMMARY

In accordance with the present invention a soft contact lens manipulating device comprises a flat, annular terminus, a hollow shank adjacent the terminus, and a pliable, vacuum actuating bulb element possessing an internal cavity completing the opposite end of the shank.

DESCRIPTION

Figure 1:
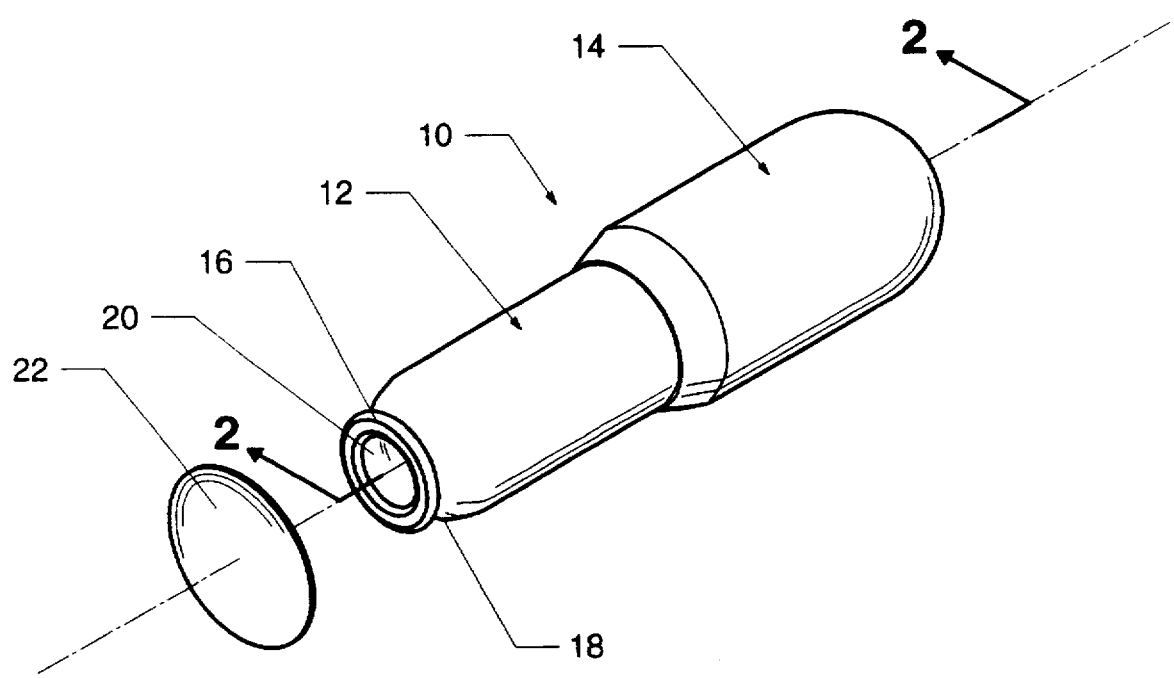
FIG. 1 is a perspective view of the novel soft contact lens manipulating device of the present invention.
Figure 2:
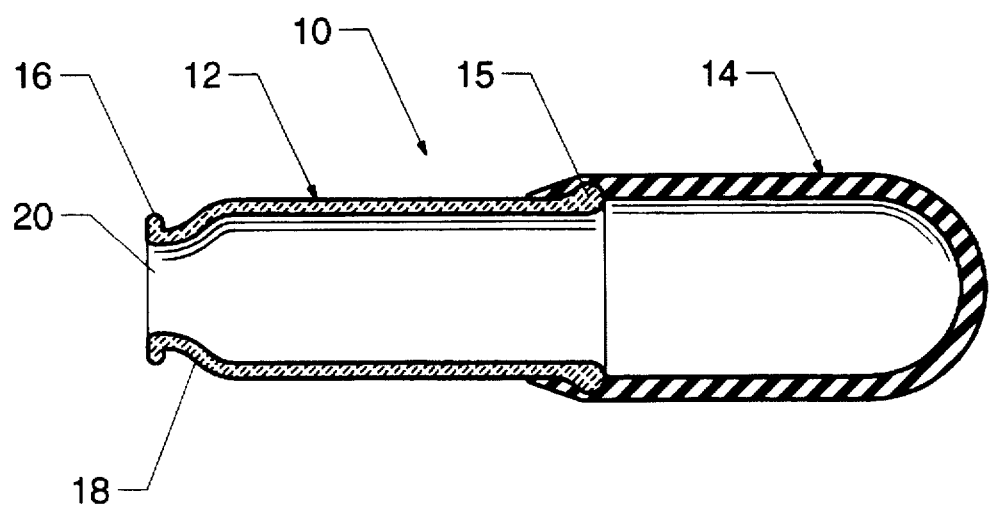
FIG. 2 is a longitudinal, vertical, cross section viewed upon the line 2—2 of FIG. 1.

FIGS. 1 and 2

The preferred embodiment of the novel soft contact lens manipulating device of the present invention is depicted in FIG. 1. The numeral 10 generally designates the device in its entirety of which its two correlative parts, a vacuum actuating bulb 14 and a shank 12, are described herein. At one end of device 10 is vacuum actuating bulb 14 which possesses an internal cavity and is constructed of thin walled pliable rubber or like material. Vacuum bulb 14 is snap lock fastened over an outward—annular shoulder 15 of shank 12. Shank 12 is molded from a suitable rigid plastic such as poly-vinyl-chloride (PVC-hyphens inserted here to facilitate pronunciation). Shank 12 maintains a thin wall construction throughout its length and provides a longitudinal duct which centrally opens outwardly at its principal end, namely, a duct opening 20. The other end of shank 12 diametrically opens interiorly through outward—annular shoulder 15 into vacuum bulb 14. Duct opening 20 is complimented with a flat—annular terminus 16 which includes an inside diameter measuring five millimeters or like size. Terminus 16 originates from an incurvate shoulder 18 extended from shank 12. The annular surface of terminus 16 typically measures two millimeters in width upon its compass. A soft contact lens 22 is shown in close proximity to device 10.

FIG. 2 illustrates a cross-sectional view of device 10. The snap lock fastening of bulb 14 to shank 12 is accomplished via a fitting of bulb 14 over an outward-annular shoulder 15 of shank 12. The view references the degree of hollowness of vacuum bulb 14 and shank 12 as depicted by the use of hatching. The thin walled construction of the bulb and the shank are additionally evident in the cross-sectional view of FIG. 2.

OPERATION

FIG. 3

Figure 3:
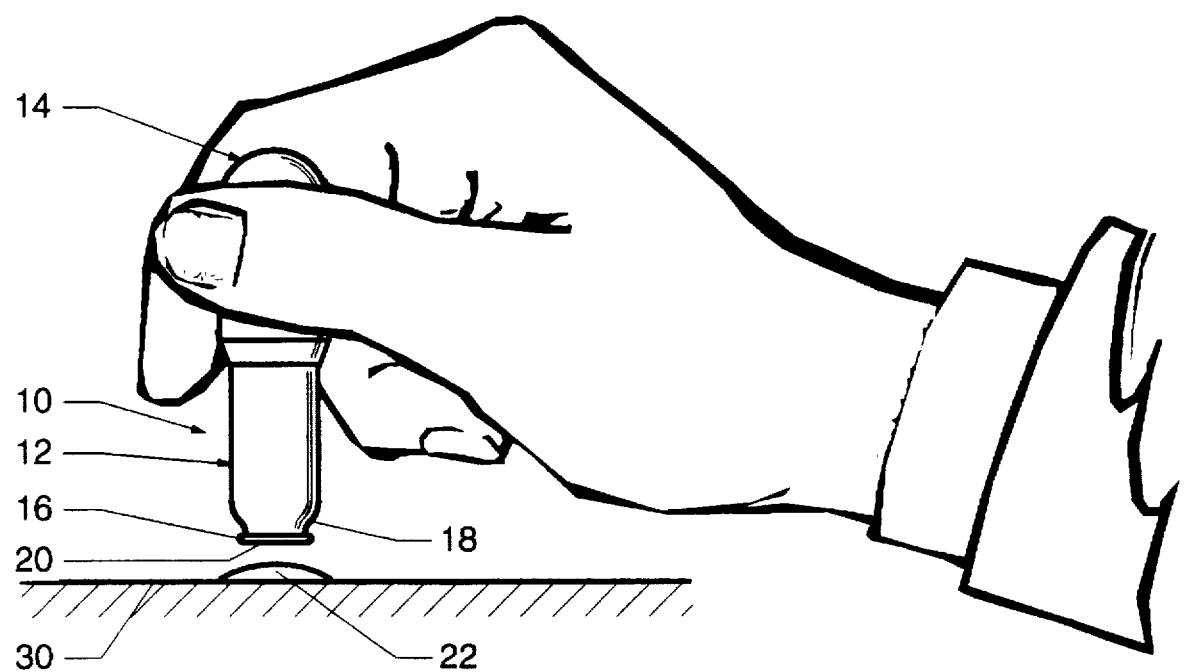
FIG. 3 is a side elevation view of the soft contact lens manipulating device involved in the intended process of engaging a soft contact lens.

The operation of the novel soft contact lens manipulating device initially involves a user arranging a suitable grasp of the device. The user will take hold of bulb 14 between their thumb and forefinger in the same manner a person would grip a conventional eyedropper as shown in FIG. 3. As the user raises device 10 from its recumbent surface utilizing the grasp described, the device is brought to a vertical position with terminus 16 disposed lowermost. Thereafter, bulb 14 may be fully compressed between the thumb and forefinger thereby expelling air from the bulb through shank 12 and out opening 20. While the user maintains the compressed state of bulb 14, device 10 is lowered along an axis perpendicular to a subject soft contact lens 22 which has been positioned on a flat aseptic surface 30 with the convex side of the lens facing up. The device is lowered to a point which terminus 16 contacts the apex of the convex side of lens 22 as depicted in FIG. 3. Upon contact, the user provides partial compression release of bulb 14 thereby creating a vacuum engagement of lens 22. The vacuum engagement of the lens is facilitated by the urge of bulb 14 to resile within a state of equalized atmospheric pressure following the partial release thereby pulling air inversely through the duct of shank 12 with air originating from opening 20. A vacuum effect is created from the inverse flow of air through opening 20 and hence, provides a force of attraction to engage a contact lens disposed in the proximity of terminus 16.

The novelty of terminus 16 is comprised of its ability to kiss the apex of the convex side of the soft contact lens during the engagement process devoid of any deformation of the lens. The area within the circumference of opening 20 within terminus 16 is of substantial size, five millimeters or the like, to securely engage the apex of the soft lens' convex side although minor in size relating to its ability to prevent the lens from collapsing and thus deforming. Without the occurrence of deformation of the soft contact lens, the user is enabled to confidently and comfortably proceed with the insertion of the lens upon the cornea of the eye.

Following the vacuum engagement of the contact lens, the user may lift device 10 accompanied by lens 22 along an axis perpendicular to surface 30. Thereafter, device 10, with lens 22 disposed outermost, can be moved and positioned within an axis perpendicularly opposed to the user's eye. As the user facilitates ease by facing a mirror thus casting their reflection of the process, the user then assists the eyelids of the subject eye open with their opposite thumb and forefinger and proceeds with device 10 coupled with the lens to a point that the lens contacts the cornea of the eye. Upon contact with the eye, the user fully compresses bulb 14 which breaks the vacuum engagement of device 10 and lens 22 thereby releasing the lens to the eye. After release of the lens upon the eye, device 10 is drawn away from the proximity of the eye along the axis perpendicular to the eye thence completing the process.

CONCLUSION, RAMIFICATIONS, AND SCOPE

Accordingly, the reader will see that the soft contact lens manipulating device can be used to grasp a soft contact lens, can be used to carry the lens to the cornea of the user's eye, and can facilitate insertion of the lens upon the cornea without encountering any deformation of the lens throughout the entire process. The feature of the device which ensures against deformation of the soft contact lens is manifest in the novel design of flat annular terminus 16. Terminus 16 achieves a confident grasp of the soft contact lens by kissing the apex of the lens' convex side. This feature obviates the need to provide a terminus which envelops the majority of the area of the lens' convex side in order to achieve engagement of the lens as presented in the prior art. Accordingly, with the use of the device of the present invention, virtually all of the lens is available to make contact upon the user's cornea without any interference resulting from the terminus of the device accidentally shifting off of the lens and touching the user's eye. Furthermore, the soft contact lens manipulating device described herein has the additional advantages in that it provides a device comprised of only two parts which is less intimidating to the user and enables the user a quicker mastery of its intended use;

it provides a simpler device in which to manufacture reducing production costs and thence, proving less expensive to the consumer; and it provides easier cleaning at frequent intervals ensuring an aseptic quality.

While the foregoing description illustrates the principles of the preferred embodiment of the invention, it will be obvious to those skilled in the art that modifications and changes may be made without departing from its intended purpose. For example, the bulb and/or the shank can have variations in their shape, length, width, degree of hollowness, etc.

Therefore, the scope of the invention should be determined by the appended claims and their legal requirements, rather than by the illustration documented hereinabove.

I claim:

1. A soft contact lens manipulating device for engaging and inserting a soft contact lens having a concave side and a convex side upon the cornea of a user's eye, comprising the combination of:

(a) a flat, annular terminus representing an improved lens seat of said device for engaging and holding said contact lens (b) a hollow shank connected to said annular terminus by an incurvate shoulder (c) a pliable, vacuum actuating bulb possessing an internal cavity attached to an opposite end of said hollow shank with the attachment accomplished by said vacuum actuating bulb enveloping in snap lock manner over an outward, annular shoulder of said hollow shank (d) the hollowness of said hollow shank providing a passageway for air to move through both ends thereof with said air communicated into or out of said vacuum actuating bulb at the one end of said hollow shank and said air entering or exiting said annular terminus at the opposite end of said hollow shank and wherein (e) said air is actuated by compressing or releasing said vacuum actuating bulb whereby a negative or positive, respectively, vacuum is established and communicated through the entirety of said device, therefore culminating at said annular terminus with said vacuum providing a mode for engaging or releasing said contact lens.

2. The device of claim 1 wherein said annular terminus engages and holds said contact lens upon the apex of the convex side thereof.

3. The device of claim 2 wherein said annular terminus provides prevention means for safeguarding against accidental contact of said annular terminus with the eye of the user.

4. The device of claim 1 wherein said annular terminus features an opening having a predetermined diameter in accord with the diameter of the apex of said convex side of said contact lens thereby providing antideformation means for preventing said lens from deforming when engaged with said annular terminus.

5. The device of claim 1 wherein said hollow shank and said vacuum actuating bulb are of two part construction in the entirety of said device.

* * * * *